United States Patent
Newell et al.

[11] Patent Number: 5,968,486
[45] Date of Patent: Oct. 19, 1999

[54] COMPOSITION FOR LIGHTENING AND HIGHLIGHTING HAIR

[75] Inventors: Gerald Newell, Hoffman Estates; Margie Fowler, Elgin, both of Ill.

[73] Assignee: Helene Curtis, Inc., Chicago, Ill.

[21] Appl. No.: 08/854,829

[22] Filed: May 12, 1997

[51] Int. Cl.$^6$ ..................................... A61K 7/135
[52] U.S. Cl. .................. 424/62; 424/70.1; 424/70.24
[58] Field of Search .......... 424/62, 70.1, 70.24, 424/401

[56] References Cited

U.S. PATENT DOCUMENTS

| | | | |
|---|---|---|---|
| 3,912,446 | 10/1975 | Zviak et al. | 8/10.1 |
| 4,517,174 | 5/1985 | Jacquet et al. | 424/62 |
| 4,983,383 | 1/1991 | Maksimoski et al. | 424/70 |
| 5,578,541 | 11/1996 | Jackson et al. | 514/547 |

OTHER PUBLICATIONS

Rieger, "Surfactants in Cosmetics", pp. 270–275 (1985).
Harry's Cosmeticology, Seventh edition, Edited by Wilkinson et al. pp. 432, 433, 454, 459 (1982).

*Primary Examiner*—Jyothsna Venkat
*Attorney, Agent, or Firm*—Matthew Boxer

[57] ABSTRACT

There is described a shampoo composition for lightening and highlighting hair which comprises
  (i) a peroxygen compound; and
  (ii) an anionic sulfonate;
    said composition having a pH less than 5. There is also described an invention directed to a method for lightening and highlighting hair which comprises. shampooing the hair with a lightening and highlighting effective amount of a composition of the invention.

11 Claims, No Drawings

COMPOSITION FOR LIGHTENING AND HIGHLIGHTING HAIR

FIELD OF THE INVENTION

The present invention is directed to a shampoo composition for lightening and/or highlighting hair.

BACKGROUND OF THE INVENTION AND PRIOR ART

It is known within the art to lighten and highlight hair with a peroxygen compound such as hydrogen peroxide. But, compositions for lightening and highlighting the hair have not been included in shampoos, since peroxygen compounds like hydrogen peroxide, are not stable in shampoos. An object of the present invention, is to provide shampoos which contain stable peroxygen compounds and thus can be used as hair lighteners and highlighters as well as shampoos.

Current products on the market for lightening hair come in two forms. The first is a spray leave-on peroxide solution. This product is used occasionally when the hair will be exposed to sunlight after application. Examples of such products include SUPER SUN-IN, SUPER WITH LEMON SUN-IN, and GRADUAL SUN-IN FOR MEN. SUPER SUN-IN has about 1.9% hydrogen peroxide at a pH of about 4.0. SUPER WITH LEMON SUN-IN has about 3.7% hydrogen peroxide at a pH of about 4.0. And GRADUAL SUN-IN FOR MEN has about 3.7% hydrogen peroxide at a pH of about 3.

The second product for lightening hair is a system which has two components: a bleaching component such as hydrogen peroxide and another component which is a bleach oil.

It is known to prepare an unstable composition by combining a bleach with a shampoo and immediately thereafter applying the resulting composition to the hair. This is usually done in a hair salon and will result in the immediate lightening of the hair. By contrast, stable shampoo compositions which gradually lighten and highlight the hair and which can easily be used at home are provided by the present invention.

Rieger, Surfactants in Cosmetics, at page 271, notes that shampoo formulations based on alpha-olefin sulfonates have exhibited excellent stability over a wide pH range and specifically at low pH's have demonstrated excellent hydrolytic stability as compared to shampoos employing alkyl and alkyl ether sulfates as the surfactants, which are completely hydrolyzed at pH 2 after 3 months at 55° C.

Harry's Cosmetology, seventh edition, indicates at page 433 that alpha-olefin sulfonates have excellent stability which should provide a broad range of use particularly for building shampoos of low pH. However, Harry's Cosmetology at page 459 suggests that low pH's for shampoos are between 5 and 7. No mention is made of shampoos having a pH of lower than 5. Moreover, no mention is made of incorporating hydrogen peroxide into a shampoo and then shampooing over a number of days to gradually achieve the hair lightening and hair highlighting desired.

Stache, Anionic Surfactants at page 520, notes that disodium lauryl sulfosuccinate DLAS which is a surfactant commonly used in shampoos, dramatically degrades at pH 5 in less than 8 weeks.

SUMMARY OF THE INVENTION

The invention relates to a shampoo composition for lightening and highlighting hair which comprises
(i) a peroxygen compound; and
(ii) an anionic surfactant which is stable to acid hydrolysis;
said composition having a pH of less than 5.0.

The invention is also directed to a method for lightening and highlighting hair which comprises administering to the skin and hair a lightening and highlighting effective amount of wt. %), in combination with an anionic surfactant meeting the proper stability requirements (preferably sulfonates, and more preferably α-olefin sulfonates present at about 5 to about 60 weight %), at a pH of less than 5, preferably about 2–4.5. The composition is made acidic by addition of a acid, such as a mineral acid, like phosphoric acid or sulfuric acid.

The peroxygen compound makes the shampoo composition a lightening and hair highlighting composition. Peroxygen compounds are not stable in shampoos at pH's of 5 and above, so that in the past hydrogen peroxide has been mixed with bleach oil at a high pH and used immediately to lighten hair. A composition of the invention.

DETAILED DESCRIPTION OF THE INVENTION

There are two methods to lighten and/or highlight hair. The first method is to deposit onto the hair, molecules which color the hair. The second method is to bleach the natural pigment found in the hair. The present invention relates to the latter method.

Hair contains a number of different pigments, principally brown and red. When hair is bleached by chemicals or the sun, the brown pigments react faster, and therefore disappear faster than the red pigments. The change in the red to brown ratio changes the appearance of the hair giving more red shading to the natural color of the hair. This results in the lightening of the hair. The red color that appears is perceived as highlighting of the hair.

Peroxygen compounds have been used to bleach human hair. A preferred peroxygen compound is hydrogen peroxide. Hydrogen peroxide is stable, but will decompose under appropriate conditions to form water and an active species of oxygen. The active species of oxygen is very reactive. It attacks and decolorizes the hair pigment.

It has surprisingly been found that a peroxygen compound, preferably hydrogen peroxide, is stable in a shampoo composition when present in about a 0.01 wt. % to about 10 wt. % (preferably 2%).

Use of shampoo compositions which have pH's of below 5 stabilizes the peroxygen compound (which can be hydrogen peroxide) which is included in said compositions.

In the compositions of the present invention, any acid that can result in a pH below 5 may be employed. More specifically, any acid which has a pK such that it can be used to obtain a composition with a pH below 5, may be employed. Exemplary of such acids are any mineral acid such as sulfuric acid or phosphoric acid. Appropriate organic acids such as citric acid may also be used.

An anionic surfactant stable to acid hydrolysis, such as a sulfonate, and more preferably an -olefin sulfonate, like sodium C14–C16 alpha-olefin sulfonate, is included in the shampoo.

The following materials may be optionally included in the compositions of the invention.

Viscosity agents may optionally be included in the compositions of the invention. Such viscosity enhancing agents are, for example, sodium alginate, gum arabic, cellulose derivatives such as methylcellulose, hydroxyethylcellulose, hydroxypropylmethylcellulose and carboxy methylcellulose, and various polymeric thickeners, such as acrylic acid derivatives. It is also possible to use inorganic thickeners, such as bentonite. These thickeners, when included, preferably are present in an amount from about 0.1% to about 10% by weight and, in particular, from about 0.5% to about 3% by weight, based on the total weight of the composition A foam enhancer, that is compatible with the low pH system of this invention, such as lauramine oxide, may also be included to improve the foaming performance of compositions of the invention.

A conditioning agent such as: polyquaternium-10 and polymer JR 30M; and other common conditioning agents including but not limited silicones, cationic polymers, humectants and moisturizers.

Other common cosmetic additives which can be incorporated into the shampoo compositions of the present invention, as long as the acidic property of the shampoo compositions is not substantially adversely affected, include, but are not limited to, fragrances, dyes, opacifiers, including fatty esters and latexes; pearlescing agents, dandruff control agents, hydrotropes, foam stabilizers, solubilizers, thickeners, preservatives, water softening agents, and the like. These optional components and additives will usually be present in weight percentages of less than about 2% each, and about 5% to about 10% in total.

The shampoo compositions of the invention can also include emulsifiers, inorganic salts, humectants, and similar materials to provide esthetic properties and desirable physical properties to the compositions. Generally, such optional ingredients are present in the compositions in weight percentages ranging from about 0.1% to about 10% each, and from about 0.1% to about 20% in total relative to the total weight of the composition.

The compositions of the present invention can be liquids, solutions, suspensions, dispersions, creams, gels, lotions, sols, mousses and the like.

Lightening and/or highlighting the hair with the compositions of the invention is carried out by shampooing the hair, that is, (1) applying water to said hair; (2) applying to said hair a lightening and highlighting effective amount of a composition of the invention, (3) lathering; and (4) rinsing said hair with water. Each application of a composition of the invention results in a small degree of lightening and/or highlighting of the hair. (Alternately, steps 1 and 2 above may be reversed, or steps 1 and 2 may be preformed simultaneously.) By using a composition of the invention on a daily basis, the hair can be gradually lightened and highlighted until it reaches the desired state. At that point, shampooing with a composition of the invention is ceased, and hair of the desired color has been obtained until it grows out.

A person who uses the shampoo compositions of the invention and also spends time in the sunlight may achieve hair lightening and/or hair highlighting more quickly than someone who uses the compositions of the invention but does not spend time in the sunlight. This is due to the additive effects of the bleaching of hair by sunlight and the chemical action of the shampoo compositions of the invention.

It will also be appreciated that the compositions of the invention have the advantage of enabling the user to obtain just the degree of highlighting and/or lightening that he or she desires at which point shampooing of the hair with the compositions of the invention is stopped, and this desired hair coloring will remain until the hair grows out.

Usually, some lightening or highlighting of the hair will be noticeable within the first ten to fourteen consecutive days of shampooing with a composition of the invention. Often, a composition of the invention will be used for up to about thirty consecutive days. However, as mentioned above, an advantage of the invention, is that a composition of the invention may be employed for more or less consecutive days than listed above, as desired by the user. In addition, the shampoo compositions may be employed every other day, or at even greater intervals as desired. If compositions of the invention are not employed on consecutive days, use may be made of the consumer's customary non-bleaching shampoo on the days when the bleaching shampoo of the invention is not being used.

It will also be appreciated that the shampoo compositions of the invention also have the benefit of cleaning the hair at the same time as lightening or highlighting the hair. The compositions of the invention also lather well and have acceptable sensory qualities.

Compositions of the invention were used as shampoos and were evaluated by a trained panel of observers and found to lighten and highlight hair.

General Procedure for Preparing Compositions of the Invention

Materials and chemicals used in the preparation of the compositions of the invention are either known or can be prepared according to known methods. A list of components of compositions of the invention is as follows:

the solvent carrier is water.

conditioning agents, more specifically conditioning polymers selected from the group consisting of Polyquaternium-10, PolymerJR 30 and the like areemployed. Mixtures of the above polymers may also be employed.

the surfactant is sodium C14-Cl6 alpha olefin sulfonate.

the viscosity agent may be lauryl alcohol.

opacifiers selected from the group consisting of ethylene glycol monostearate and ethylene glycol distearate may optionally be employed.

a foaming agent which is stable under low pH conditioners, such as lauramine oxide may be employed.

a mineral acid such as phosphoric acid or sulfuric acid is employed.

a preservative such as DMDM hydantoin may be employed.

viscosity agent such as a salt like sodium chloride and ammonium chloride may be employed.

a solubilzer/humectant such as propylene glycol may be employed.

a fragrance stable at low pH may be employed. Other cosmetic additives may be employed as well.

a peroxy compound such as hydrogen peroxide may be employed.

Materials from the above list are used in the general description of the preparation of the compositions of the invention which is set forth just below.

Compositions of the Invention are prepared as follows:

Step 1. The solvent carrier, water, is added to a suitably sized tank.

Step 2. Moderate agitation is begun.

Step 3. Polymers, such as Polyquaternium-10 and PolymerJR 30 are added and mixed until dissolved.

Step 4. Surfactants, foam enhancers, viscosity increasing enhancers, are added and mixed until dissolved.

Step 5. An acid such as phosphoric acid or sulfuric acid, added and mixed until dissolved and the batch is at uniform pH.
Step 6. Any and all cosmetic additives are added.
Step 7. Hydrogen peroxide is added and mixed until the batch is uniform.

The above seven steps are done at about room temperature. If an opacifier is to be included to the composition being prepared, it is done in the following way: First the composition right after step 4, above, is heated to about 160° F., the opacifier is added and the composition is stirred until the opacifier is dissolved, and then the resulting composition is cooled to about 110° F. Preparation of the composition is continued with step 5 above.

Shampoo compositions of the present invention have passed stability tests in a three month study at 35° F., room temperature, and 110° F. These stability tests checked the compositions for color, odor, appearance, pH, viscosity, and level of hydrogen peroxide present.

A description of the preparation of compositions of the invention follows.

Example 1

| Description | % |
| --- | --- |
| Water | QS |
| Polyquaternium-10 | 0.525 |
| Polymer JR 30M | 0.3 |
| Sodium C14–C16 Olefin Sulfonate | 35 |
| Lauryl Alcohol | 0.5 |
| Ethylene Glycol Monostearate | |
| Ethylene Glycol Distearate | |
| Lauramine Oxide | 3.7 |
| Phosphoric Acid | 1 |
| Sulfuric Acid | |
| DMDM Hydantoin | 0.1 |
| Propylene Glycol | |
| Sodium Chloride | 0.8 |
| Ammonia Chloride | |
| Fragrance | 0.6 |
| Hydrogen Peroxide, 35% | 4.6 |
| pH | 3 |
| Viscosity (cps) | 3900 |

A composition of the invention was prepared using the above materials and carrying out the following steps:

1. Water was added to a suitably sized tank.
2. The water was agitated and both polymers were added. Mixing was continued until the mixture was uniform.
3. Sodium C14–C16 alpha olefin sulfonate was added and mixed until the composition was uniform.
4. Lauryl alcohol was added and mixed for 15 minutes.
5. Lauramine Oxide was added.
6. Phosphoric acid was added.
7. DMDM hydantoin was added.
8. Sodium Chloride was added.
9. Fragrance was added and mixed for 15 minutes.
10. The viscosity and pH were checked and then hydrogen peroxide was added.

The following examples show compositions of the invention which were prepared in a manner similar to that above. These examples show compositions with different values for pH, viscosity, detergent level, with and without opacifiers, with different mineral acids, different amounts of hydrogen peroxide, with and without viscosity agents, and with and without conditioning agents. These examples are illustrative of composions of the invention; however, the invention is not limited by these examples.

Example 2

| Description | |
| --- | --- |
| Water | QS |
| Polyquaternium-10 | 0.525 |
| Polymer JR 30M | 0.3 |
| Sodium C14–C16 Olefin Sulfonate | 51 |
| Lauryl Alcohol | 0.5 |
| Ethylene Glycol Monostearate | 1 |
| Ethylene Glycol Distearate | |
| Lauramine Oxide | 5.4 |
| Phosphoric Acid | 1.1 |
| Sulfuric Acid | |
| DMDM Hydantoin | 0.1 |
| Propylene Glycol | |
| Sodium Chloride | 0.6 |
| Ammonia Chloride | |
| Fragrance | 0.6 |
| Hydrogen Peroxide, 35% | 5.1 |
| pH | 2.8 |
| Viscosity (cps) | 3200 |

Example 3

| Description | |
| --- | --- |
| Water | QS |
| Polyquaternium-10 | |
| Polymer JR 30M | 0.8 |
| Sodium C14–C16 Olefin Sulfonate | 45 |
| Lauryl Alcohol | 0.5 |
| Ethylene Glycol Monostearate | |
| Ethylene Glycol Distearate | 1 |
| Lauramine Oxide | 4.8 |
| Phosphoric Acid | |
| Sulfuric Acid | 0.8 |
| DMDM Hydantoin | 0.1 |
| Propylene Glycol | |
| Sodium Chloride | |
| Ammonia Chloride | 0.4 |
| Fragrance | 0.6 |
| Hydrogen Peroxide, 35% | 5.1 |
| pH | 2.9 |
| Viscosity (cps) | 4500 |

Example 4

| Description | |
| --- | --- |
| Water | QS |
| Polyquaternium-10 | 1 |
| Polymer JR 30M | |
| Sodium C14–C16 Olefin Sulfonate | 45 |
| Lauryl Alcohol | 0.5 |
| Ethylene Glycol Monostearate | |
| Ethylene Glycol Distearate | |
| Lauramine Oxide | 4.8 |
| Phosphoric Acid | 1 |
| Sulfuric Acid | |
| DMDM Hydantoin | 0.1 |
| Propylene Glycol | 1 |
| Sodium Chloride | |
| Ammonia Chloride | 0.4 |
| Fragrance | 0.6 |
| Hydrogen Peroxide, 35% | 4 |
| pH | 3 |
| Viscosity (cps) | 4800 |

Example 5

| Description | |
|---|---|
| Water | QS |
| Polyquaternium-10 | 0.525 |
| Polymer JR 30M | 0.3 |
| Sodium C14–C16 Olefin Sulfonate | 40 |
| Lauryl Alcohol | 0.5 |
| Ethylene Glycol Monostearate | |
| Ethylene Glycol Distearate | |
| Lauramine Oxide | 4.2 |
| Phosphoric Acid | 0.8 |
| Sulfuric Acid | |
| DMDM Hydantoin | 0.1 |
| Propylene Glycol | |
| Sodium Chloride | 1 |
| Ammonia Chloride | |
| Fragrance | 0.6 |
| Hydrogen Peroxide, 35% | 4.6 |
| pH | 3.3. |
| Viscosity (cps) | 6200 |

Example 6

| Description | |
|---|---|
| Water | QS |
| Polyquaternium-10 | |
| Polymer JR 30M | |
| Sodium C14–C16 Olefin Sulfonate | 51.5 |
| Lauryl Alcohol | 0.5 |
| Ethylene Glycol Monostearate | |
| Ethylene Glycol Distearate | |
| Lauramine Oxide | 5.4 |
| Phosphoric Acid | 1 |
| Sulfuric Acid | |
| DMDM Hydantoin | 0.1 |
| Propylene Glycol | |
| Sodium Chloride | 1 |
| Ammonia Chloride | |
| Fragrance | 0.6 |
| Hydrogen Peroxide, 135% | 2.9 |
| pH | 3.1 |
| Viscosity (cps) | 3250 |

Example 7

| Description | |
|---|---|
| Water | QS |
| Polyquaternium-10 | 0.525 |
| Polymer JR 30M | 0.3 |
| Sodium C14–C16 Olefin Sulfonate | 45 |
| Lauryl Alcohol | 0.5 |
| Ethylene Glycol Monostearate | |
| Ethylene Glycol Distearate | 1 |
| Lauramine Oxide | 4.8 |
| Phosphoric Acid | 1 |
| Sulfuric Acid | |
| DMDM Hydantoin | 0.1 |
| Propylene Glycol | |
| Sodium Chloride | 0.6 |
| Ammonia Chloride | |
| Fragrance | 0.6 |
| Hydrogen Peroxide, 35% | 5.1 |
| pH | 2.9 |
| Viscosity (cps) | 3850 |

Example 8

| Description | |
|---|---|
| Water | QS |
| Polyquaternium-10 | |
| Polymer JR 30M | |
| Sodium C14–C16 Olefin Sulfonate | 45 |
| Lauryl Alcohol | 0.5 |
| Ethylene Glycol Monostearate | 0.8 |
| Ethylene Glycol Distearate | |
| Lauramine Oxide | 5.4 |
| Phosphoric Acid | 1 |
| Sulfuric Acid | |
| DMDM Hydantoin | 0.1 |
| Propylene Glycol | |
| Sodium Chloride | 0.8 |
| Ammonia Chloride | |
| Fragrance | 0.6 |
| Hydrogen Peroxide, 35% | 4.85 |
| pH | 3 |
| Viscosity (cps) | 4250 |

All of the above compositions of the invention have passed stability tests in a three month study at 35° F., room temperature, and 110° F. These tests checked the compositions for color, odor, appearance, pH, viscosity, and the level of hydrogen peroxide.

Experiments were run which demonstrated that hydrogen peroxide was not stable at high pHs, that is pHs of 5 to 7 which are currently being used in shampoo technology. For example, a typical shampoo composition was made at pH 5.4 using a mixture of ammonium lauryl sulfate and ammonium lauryl ether sulfate as the detergent system, and it had an initial hydrogen peroxide level of 1.58% After one month at 110° F. the peroxide level dropped to 1.44%. This shows the instability of hydrogen peroxide in a typical current shampoo composition at a typical pH.

Experiments were also run with a typical shampoo composition using a mixture of ammonium lauryl sulfate and ammonium lauryl ether sulfate as the detergent system, adjusted to a low pH. In this case, on storage, the viscosity dropped and pH increased. For example the above composition was made and adjusted to a pH 2.85 and the viscosity was 8290 cps. After one month at 110° F., the pH increased to 3.50 and the viscosity dropped to 5380 cps. This shows the instablity of a current shampoo detergent system at low ph.

What is claimed is:

1. A composition for lightening and highlighting hair comprising;
   (i) hydrogen peroxide from about 0.1 to about 10.0 wt. %; and
   (ii) an α-olefin sulfonate from about 5 to about 60 wt. %; said composition having a pH from about 2–4.5.

2. The composition according to claim 1, wherein the α-olefin sulfbnate is sodium α-olefin sulfonate.

3. The composition according to claim 1, wherein the hydrogen peroxide is present at about 2 wt. %.

4. A composition according to claim 1, which further comprises a foam enhancer, lauramine oxide.

5. A composition according to claim 1 which further comprises a viscosity enhancer, lauryl alcohol.

6. A composition according to claim 1, wherein the pH is lowered by addition of a mineral acid selected from the group consisting of phosphoric acid and sulfuric acid.

7. A method for lightening and highlighting hair which comprises:

(1) applying water to said hair;
(2) applying to said hair a lightening and highlighting effective amount of composition comprising:
   (i) hydrogen peroxide from about 0.1 to about 10.0 wt. %; and
   (ii) an α-olefin sulfonate from about 5 to about 60 wt. %.
said composition having a pH from about 2–4.5;
(3) lathering; and
(4) rinsing said hair with water.

8. The method according to claim 7, wherein the hydrogen peroxide is present at about 2 wt. %.

9. A method according to claim 7, which further comprises a foam enhancer, lauramine oxide.

10. A method according to claim 7, which further comprises a viscosity enhancer, lauryl alcohol.

11. A method according to claim 7, wherein the pH is lowered by addition of a mineral acid selected from the group consisting of sulfuric acid and phosphoric acid.

* * * * *